United States Patent [19]

Bishop et al.

[11] Patent Number: 5,681,959
[45] Date of Patent: Oct. 28, 1997

[54] CHEMICAL SYNTHESIS OF AZAINDOLES

[75] Inventors: Brian Cchristopher Bishop, Bishops Stortford; Ian Frank Cottrell, Hertford; Mark Cameron, Bishops Stortford; David Hands, London, all of England

[73] Assignee: Merck, Sharp & Dohme Ltd., Hertfordshire, England

[21] Appl. No.: 604,133

[22] Filed: Feb. 20, 1996

[30] Foreign Application Priority Data

Feb. 21, 1995 [GB] United Kingdom ............... 9503400.5
Oct. 27, 1995 [GB] United Kingdom ............... 9522015.8

[51] Int. Cl.$^6$ ................................................ C07D 471/04
[52] U.S. Cl. ................................................ 546/113
[58] Field of Search ................................................ 546/113

[56] References Cited

U.S. PATENT DOCUMENTS

| | | | |
|---|---|---|---|
| 3,362,956 | 1/1968 | Archer et al. | 544/363 |
| 3,511,841 | 5/1970 | Archer et al. | 544/362 |
| 5,212,195 | 5/1993 | Clark et al. | 514/381 |
| 5,432,177 | 7/1995 | Baker et al. | 514/253 |

FOREIGN PATENT DOCUMENTS wo94/20497   9/1994   WIPO.

OTHER PUBLICATIONS

Lorenz et al. J. Organic Chem. 1965, 30, 2531–2533.
Estel et al. J. Organic Chem. 1988, 53, 2740–2744.
Sakamoto et al. Heterocycles 1992, 34, 2379–2384.
Clark et al. Synthesis 1991, 87–88.

*Primary Examiner*—Bernard Dentz
*Attorney, Agent, or Firm*—Robert J. North; Melvin Winokur

[57] ABSTRACT

The present invention relates to a process for the preparation of azaindole derivatives of the formula

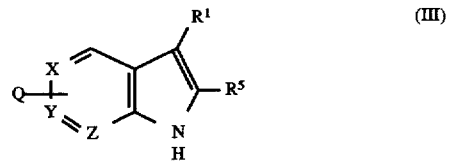

wherein Q is hydrogen, $C_{1-6}$alkyl, $C_{2-6}$alkenyl, $C_{1-6}$alkoxy, hydroxy, aryl or aryl$C_{1-4}$alkyl;

one of X, Y and Z is —N= and the others are —CH=;

$R^1$ is hydrogen, $C_{1-6}$alkyl, $C_{2-6}$alkenyl or $C_{1-6}$alkyl substituted by a group selected from aryl or —NR$^2$R$^3$ where $R^2$ and $R^3$ each independently represent $C_{1-4}$alkyl, or $R^2$ and $R^3$, together with the nitrogen atom to which they are attached, form a 4–7 membered saturated heterocyclic ring, optionally containing in the ring an oxygen or sulphur atom or a group NR$^4$ where $R^4$ is $C_{1-4}$alkyl, aryl or aryl$C_{1-4}$alkyl; and $R^5$ is a hydrogen atom or a group selected from $C_{1-6}$alkyl or aryl.

20 Claims, No Drawings

CHEMICAL SYNTHESIS OF AZAINDOLES

The present invention relates to a process for the preparation of azaindole derivatives which are useful as intermediates in the preparation of certain therapeutic agents. In particular, the present invention provides a short and efficient process for the preparation of 5-, 6- and 7-azaindoles in high overall yield.

7-Azaindole (also known as 1H-pyrrolo[2,3-b]pyridine) and derivatives thereof have been prepared by a variety of approaches:

Lorenz et al (*J. Org. Chem.*, 1965, 30, 2531) describe a modified Madelung synthesis which comprises cyclization of N-(3-methyl-2-pyridyl)-N'-methyl-N'-phenylformamidine in the presence of sodium N-methylanilide in boiling N-methylaniline (198° C.) to give 7-azaindole. This process suffers from several major disadvantages. High temperatures are required in three stages, three vacuum distillations are required and the final product isolation involves crystallisation and distillation/sublimation.

Estel et al (*J. Org. Chem.*, 1988, 53, 2740) describe a metalation/S$_{RN}$1 coupling approach which comprises lithiation, iodination and fluorine substitution on 2-fluoropyridine to give 2-substituted-3-iodopyridines which are further subjected to iodine S$_{RN}$1 substitution with an enolate to afford ketones which are cyclized to give various substituted 7-azaindoles. This approach involves several steps, requires low temperatures and uses expensive reagents.

Sakamoto et al (*Heterocycles*, 1992, 34, 2379) describe a palladium catalysed reaction of nitropyridine derivatives with (Z)-1-ethoxy-2-tributylstannylethene followed by reduction and cyclisation. This process is particularly unsuitable for large scale manufacture of pharmaceuticals since it utilises potentially toxic organotin reagents.

Clark et al (*Synthesis*, Oct. 1991, 871) describe the preparation of 1-(tert-butoxycarbonyl)-1H-pyrrolo[2,3-b]pyridine via the intermediate 1-(tert-butoxycarbonyl)-2,3-dihydro-2-hydroxy-1H-pyrrolo[2,3-b]pyridine. The preparation of this intermediate is reported to require a low reaction temperature (−60° C.). Furthermore, it is reported that this intermediate is stable to the usual conditions of dehydration (hydrochloric acid in tetrahydrofuran).

The complexity and length of these prior art processes including their requirements for either very high or very low temperatures and their use of either expensive or potentially toxic reagents, renders these prior art syntheses impracticable when attempted on anything other than a laboratory scale. It will be appreciated that 7-azaindole and derivatives thereof are important intermediates for various classes of pharmaceutical compounds. As such, there is a need for the development of a process which is readily amenable to scale-up and hence capable of practical application to the manufacturing plant.

The present invention accordingly provides a convenient, efficient process for the synthesis of 7-azaindole and derivatives thereof which utilizes readily available and cheap reagents and which, in a minimum of steps, affords product of high purity in high overall yield.

Compared with existing technology, the process is operated over a convenient temperature range (−10° C. to +55° C.), thus no special high or low temperature facilities are required. In a further aspect of the present inventions the crude product obtained from the synthesis described herein is readily purified by crystallisation as, for example, the tartaric acid salt thereby avoiding the need for extensive purification by chromatography and distillation.

This method is equally applicable to the preparation of 5-azaindole (1H-pyrrolo[3,2-c]pyridine) and 6-azaindole (1H-pyrrolo[2,3-c]pyridine) and the derivatives thereof.

Thus, in a first aspect of the present invention, there is provided a process for the preparation of azaindole derivatives which comprises:

(i) deprotonation using 2 or more equivalents of an alkyllithium reagent of a compound of formula (I):

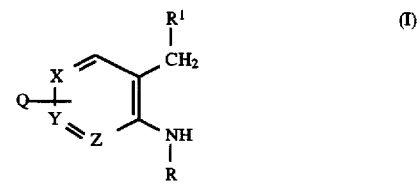

wherein

Q is hydrogen, $C_{1-6}$alkyl, $C_{2-6}$alkenyl, $C_{1-6}$alkoxy, hydroxy, aryl or aryl$C_{1-4}$alkyl;

one of X, Y and Z is —N= and the others are —CH=;

R is —CO(O)$C_{1-6}$alkyl or —C(O)$C_{1-6}$alkyl; and $R^1$ is hydrogen, $C_{1-6}$alkyl, $C_{2-6}$alkenyl or $C_{1-6}$alkyl substituted by a group selected from aryl or —NR$^2$R$^3$ where R$^2$ and R$^3$ each independently represent $C_{1-4}$alkyl, or R$^2$ and R$^3$, together with the nitrogen atom to which they are attached, form a 4–7 membered saturated heterocyclic ring, optionally containing in the ring an oxygen or sulphur atom or a group NR$^4$ where R$^4$ is $C_{1-4}$alkyl, aryl or aryl$C_{1-4}$alkyl;

(ii) reaction of the product of step (i) with an amide of formula (IIA) or an ester of formula (IIB):

wherein

R$^5$ is a hydrogen atom or a group selected from $C_{1-6}$alkyl or aryl; and

R$^6$ is $C_{1-6}$alkyl;

R$^7$ is $C_{1-6}$alkyl, $C_{1-6}$alkoxy or aryl; and

R$^8$ is $C_{1-6}$alkyl, aryl$C_{1-4}$alkyl or aryl;

(iii) reaction of the product of step (ii) with a concentrated acid to give an azaindole derivative of formula (III):

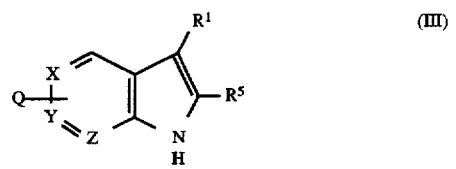

wherein Q, X, Y, Z, R$^1$ and R$^5$ are as previously defined.

According to a further aspect of the present invention, there is provided a process for the preparation of azaindole derivatives which comprises steps (i) to (iii) as defined above together with the step:

(iv) isolating the product of step (iii) as a crystalline solid by reaction with an acid to form the corresponding salt.

As used herein, the term "aryl" as a group or part or a group means unsubstituted phenyl or pyridyl, or phenyl or pyridyl substituted by one or two $C_{1-6}$alkyl, $C_{2-6}$alkenyl, $C_{1-6}$alkoxy or hydroxy groups.

Suitable alkyllithium reagents of use in step (i) above include n-butyllithium and n-hexyllithium. Preferably between 2 and 3 equivalents of alkyllithium is used. Step (i) is preferably effected at a reduced temperature, for instance between −15° C. and +15° C., and preferably between −10° C. and +5° C. The reaction is conveniently effected in an inert solvent such as an ether, for example, tetrahydrofuran.

Preferably step (ii) above is effected without prior isolation of the product of step (i). The reaction may be effected at a temperature between −15° C. and +40° C., for example, between −15° C. and +20° C., and preferably between −5° C. and +10° C.

Preferably step (ii) is effected using an amide of formula (IIA).

Suitable acids for use in step (iii) above include hydrochloric acid, sulphuric acid, phosphoric acid, trifluoroacetic acid and methanesulphonic acid. Preferably 3M to 5.5M acid is used, especially 5.5M hydrochloric acid, 5M sulphuric acid, 5M phosphoric acid and 5M aqueous trifluoroacetic acid. Preferably, the product of step (ii) is added to the acid. Preferably the reaction temperature is maintained between 0° C. and 55° C., preferably at about 10° C. and, when the quench is complete, the temperature is then allowed to rise to between 40° C. and 55° C.

Where the azaindole derivative is isolated as a crystalline solid according to step (iv) above, suitable acids include any acid with a pKa of less than or equal to 3.0, for instance, DL-tartaric acid, D-tartaric acid, L-tartaric acid, maleic acid, methanesulphonic acid and p-toluenesulphonic acid. Alternatively, a mineral acid such as hydrochloric acid may be used. Crystallisation is conveniently effected by dissolving the product of step (iii) in a suitable organic solvent, for example isopropyl acetate (IPAC), acetone or ethanol or a mixture thereof. A warm solution of the organic acid in ethanol or water is then added and the mixture stirred at a temperature between 0° C. and room temperature to effect crystallisation. The free base may be subsequently liberated by conventional means, for instance, by reaction with 5M sodium hydroxide solution.

In the compounds of formula (I) above, Q is preferably a hydrogen atom. $R^1$ is preferably a hydrogen atom. R is preferably —CO(O)-tert-butyl or —C(O)-tert-butyl, especially —CO(O)-tert-butyl.

In the compounds of formula (IIA) above, $R^5$ is preferably a hydrogen atom. Also in the compounds of formula (IIA), $R^6$ is preferably $C_{1-3}$alkyl and $R^7$ is preferably $C_{1-3}$alkyl or $C_{1-3}$alkoxy. In particular, $R^6$ and $R^7$ are preferably $C_{1-3}$alkyl groups, especially methyl groups.

In the compounds of formula (IIB) above, $R^5$ is preferably 1a hydrogen atom or a methyl group. Also in the compounds of formula (IIB), $R^8$ is preferably a $C_{1-3}$alkyl group, especially an ethyl group.

In the compounds of formula (III) above, Q is preferably a hydrogen atom. $R^1$ is preferably a hydrogen atom. $R^5$ is preferably a hydrogen atom.

The process of the present invention is preferably used for the preparation of compounds of formula (III) in which X and Y are —CH= and Z is —N=, i.e. 7-azaindole and its derivatives.

The following non-limiting examples illustrate the process according to the present invention. The following HPLC assay systems (referred to in the Examples as Method 1 and Method 2) are used:

| Method 1 | |
|---|---|
| Column: | Zorbax RX C8 25 cm × 4.6 mm |
| A: | 0.05M Potassium dihydrogen phosphate 0.015M Sodium hexane sulphonate |
| B: | Acetonitrile |
| Gradient: | 80% A to 30% A in 10 minutes 30% A for 5 minutes |
| Flow: | 1.0 ml · min$^{-1}$ |
| Detection: | UV; λ = 210/220 nm |
| Temperature: | 40/45° C. |

| Method 2 | |
|---|---|
| Column: | Ultratechsphere C8 25 cm × 4.6 mm |
| A: | 0.05M Potassium dihydrogen phosphate 0.015M Sodium hexane sulphonate |
| B: | Acetonitrile |
| Gradient: | 80% A to 30% A in 10 minutes 30% A for 5 minutes |
| Flow: | 1.0 ml · min$^{-1}$ |
| Detection: | UV; λ = 220 nm |
| Temperature: | 40° C. |

EXAMPLE 1

1H-Pyrrolo[2,3-b]pyridine a) 2,2-Dimethyl-N-(3-methyl-2-pyridinyl)propanamide 2-Amino-3-methylpyridine (108 g) and triethylamine (180 ml) were dissolved in tetrahydrofuran (500 ml) and the solution cooled to 0° C. in an acetone/ice bath. A solution of pivaloyl chloride (135.4 ml) in tetrahydrofuran (250 ml) was added over 70 minutes at such a rate that the temperature remained between 0° C. and 5° C. The mixture was aged at 0° C. for 15 minutes, allowed to warm to room temperature and aged for 3 hours. The reaction mixture was quenched into water (1 liter), the phases separated and the aqueous phase extracted with ethyl acetate (2×200 ml). The organic phases were combined, washed with saturated sodium bicarbonate solution (2×200 ml), brine (200 ml) and dried (sodium sulphate). The solvent was removed under reduced pressure and the solid residue flushed with hexane (100 ml). The solid was dissolved in hot hexane, filtered and allowed to crystallise. The title compound was collected by filtration, washed with hexane (200 ml) and dried (147.4 g, 76.8% yield; mp 90°–92° C.).

b) 1H-Pyrrolo[2,3-b]pyridine

A solution of the product of step (a) (1.92 g) in tetrahydrofuran (60 ml) was cooled to −10° C. in an acetone/ice bath and n-butyllithium (15.8 ml, 1.6M) added, via a syringe, over 10 minutes (temperature ≦2° C.). The mixture was aged at −5° to 0° C. for 4 hours. Dimethylformamide (2.5 ml) was added via a syringe over 5 minutes (temp. to 0° C.). The batch was aged at 0° C. for 40 minutes and allowed to warm to 20° C. The reaction mixture was quenched into 3M hydrochloric acid (50 ml) and the phases separated. The organic phase was extracted with 3M hydrochloric acid (1×20 ml, 1×10 ml) and the aqueous phases were combined. The aqueous phase was extracted with ethyl acetate (30 ml) and tert-butyl methyl ether (2×30 ml) and then heated on a steam bath for 8 hours. The mixture was cooled to 25° C. and neutralised by the addition of 6M sodium hydroxide solution (ca. 65 ml, temp. ≦35° C.). The product was extracted into ethyl acetate (4×20 ml), the organic phases were combined, washed with brine (25 ml) and dried (sodium sulphate). The solvent was evaporated under reduced pressure to give a yellow gum (1.3 g).

The residue was chromatographed on silica gel (60 g) eluting with ethyl acetate. The fractions containing 7-azaindole were collected and evaporated under reduced pressure to give the title compound as a yellow crystalline solid (0.7 g, 59% yield); mp 101°–103° C. [lit. 104°–105° C.].

EXAMPLE 2

1H-Pyrrolo[2,3-b]pyridine a) 2-(tert-Butoxycarbonylamino)-3-methylpyridine

To a stirred solution of di-tert-butyldicarbonate (326.2 g) in hexane (200 ml) at reflux temperature was added, over 40 minutes, a solution of 2-amino-3-methylpyridine (100 g) in ethyl acetate (50 ml). The mixture was heated at reflux for a further 10 minutes and then allowed to cool to ambient temperature (crystallisation occurred at ca. 50° C.). The suspension was diluted with hexane (300 ml) and aged for 1 hour at 20° C. The product was isolated by filtration, washed with hexane (750 ml) and dried under vacuum to give the title compound (143 g, 75% yield); mp 131°–134° C. [lit. 132°–133° C.]; Analysis Found C 63.65, H 7.79, N 13.5. $C_{11}H_{16}N_2O_2$ requires C 63.44, H 7.74, N 13.45%.

b) 1H-Pyrrolo[2,3-b]pyridine

A solution of the product of step (a) (50.0 g) in tetrahydrofuran (1.0 liter) cooled to −5° C. was treated with n-butyllithium (210 ml, 0.53 mol, 2.5M, 2.2 eq) at such a rate as to maintain the temperature ≦+2° C. On complete addition (45 minutes) the resulting deep red mixture was aged at 0° C. for 1 hour. The vigorously stirred solution was then treated with anhydrous dimethylformamide (24.2 ml, 0.3 mol, 1.3 eq.) in one portion. The resulting yellow slurry was stirred at 10° C. to room temperature over 30 minutes and then treated, rapidly, with 5.5M hydrochloric acid (250 ml). The ensuing exotherm took the temperature to 45° C. The mixture was heated at 45° to 50° C. for 1 hour, cooled to room temperature and the phases separated. The organic phase was extracted with 2M hydrochloric acid (250 ml) and the combined aqueous phases cooled to 0° C. Isopropyl acetate (250 ml) was added and the stirred mixture treated with 5M sodium hydroxide solution (250 ml) at such a rate as to maintain the temperature at ≦20° C. The mixture was stirred for 5 minutes, allowed to settle and the phases separated. The aqueous phase was extracted with isopropyl acetate (250 ml). The combined isopropyl acetate phases were washed with saturated brine (250 ml) and the isopropyl acetate solution assayed for 7-azaindole: HPLC assay= 94.7%w/w (method 2) yield=26.8 g.

c) 1H-Pyrrolo[2,3-b]pyridine—Purification

The product of step (b) in isopropyl acetate (100 ml, 26.8 g) was filtered and diluted with acetone (200 ml). A warm solution of DL-tartaric acid (34.1 g) in water (100 ml) was added in one portion. The initially cloudy solution became clear, then immediately crystollised and set solid. Acetone (100 ml) was added, the mixture broken up and the mixture stirred vigorously at 20° C. for 30 minutes. The mixture was cooled to 5° C. and aged for one hour. The product was collected by filtration, washed with acetone (3×50 ml) and dried in vacuo at 50° C. (52.5 g, 86% yield; mp 148°–150° C.).

The solid (52.3 g) was dissolved in warm water (500 ml, 50° C.) and 5M sodium hydroxide solution (45 ml) added. The solution was cooled in an ice bath and further 5M sodium hydroxide (45 ml) added over 5 minutes. The mixture was aged at 5° C. for one hour, the solid collected by filtration and washed with water (3×100 ml). The product was air dried and then dried in vacuo at 50° C. to give the title compound (20.6 g, 89.5% recovery); HPLC assay= 99%; $^1$H NMR (250 MHz, $CDCl_3$) δ4.55 (2H, s), 6.51 (1H, d, J=4 Hz), 7.12 (1H, dd, J=5.8 Hz), 7.40 (1H, d, J=4 Hz), 8.04 (1H, dd, J=2.8 Hz), 8.18 (1H, dd, J=2.5 Hz).

EXAMPLE 3

1H-Pyrrolo[2,3-b]pyridine

To a stirred solution of 2-(tert-butoxycarbonylamino)-3-methylpyridine (Example 2a) (100 g) in anhydrous tetrahydrofuran and cooled to −15° C. was slowly added hexyllithium (2.8M, 350 ml) over 40 minutes, while maintaining the reaction temperature at −15° C. The reaction mixture was aged at −15° C. for 15 minutes and then allowed to warm to −5° C. Anhydrous dimethylformamide (40 ml) was added in one portion (temp. to 5° C.) and the resulting yellow suspension vigorously stirred at ambient temperature for 30 minutes. 5.5M Hydrochloric acid (900 ml) was added in one portion and the mixture heated at 45° C. for one hour. The mixture was cooled to 20° C. and the phases separated. The aqueous phase was covered with isopropyl acetate (500 ml), cooled to 5° C. and with vigorous stirring, neutralised by the addition of sodium hydroxide pellets (200 g, 5.0 mole). The phases were separated and the aqueous phase extracted with isopropyl acetate (500 ml). The organic phases were combined, washed with 2%w/w sodium metabisulphite (2×500 ml) and evaporated to residue (56.8 g, 91%w/w purity, 91%w/w assay yield (method 1)).

The product was purified by sublimation (0.2 mmHg, 120° C.) to give the title compound (51.0 g, 96%w/w assay purity, 88% assay yield (method 1)).

EXAMPLE 4

1H-Pyrrolo[2,3-b]pyridine, L-tartrate salt a) 1H-Pyrrolo[2,3-b]pyridine

A solution of 2-(tert-butoxycarbonylamino)-3-methylpyridine (Example 2a) (104.1 g, 0.5 mol) in tetrahydrofuran (2.0 liters) was cooled to −1° C. n-Butyllithium (2.5M, 400 ml, 1.0 mol) was added over 45 minutes (temp. ≦+5° C.) and the mixture aged at 0° C. to +3° C. for 1 hour. Dimethylformamide (39.2 ml, 0.51 mol) was added in one portion (temp. −3° C. to 9.9° C.), the mixture was stirred at +6° C. to +18° C. for 1 hour. The yellow suspension was transferred by canula, over 1 hour, into cooled (2.5° C.), vigorously stirred 5.5M hydrochloric acid (500 ml) at such a rate that the temperature was maintained at ≦10° C. The flask and transfer lines were washed through with 2M hydrochloric acid (200 ml) and the stirred mixture was heated at 45°–50° C. for 2 hours.

The mixture was cooled to 20° C. and the phases separated. The aqueous phase was covered with isopropyl acetate (750 ml) and cooled to 5° C. 5M Sodium hydroxide solution (401 ml) was added over 30 minutes (temp. ≦15° C.). The phases were separated, the isopropyl acetate solution washed with saturated aqueous brine (250 ml) (56.3 g, 95.5% assay yield (method 1)).

The solvent was evaporated under reduced pressure and the residue (58.5 g) used directly in the next stage.

b) 1H-pyrrolo[2,3-b]pyridine, L-tartrate salt

The product of step (a) (58.5 g) was dissolved in warm isopropyl acetate (400 ml), the solution filtered, and added, over 15 minutes, to a warm solution (55° C.) of L-tartaric acid (75 g, 0.5 mol) in 96% ethanol (500 ml). The salt crystallised almost immediately. The slurry was cooled to 5° C. and stirred for 1 hour. The solid was collected by filtration, washed with isopropanol (2×10 ml) and dried to give the title compound (119.4 g, 89% yield; mp 165°–167°

C., HPLC assay 97.6% assay purity, >98A; assay yield= 87%) (method 1).

Following a similar procedure to that described in Example 2, the following compounds (Examples 5 to 10) have been prepared:

[Structure I → Structure III, where compound (I) has R¹–CH₂ group, NH–C(=O)–O–C(CH₃)₃ (Boc), pyridine N; compound (III) is pyrrolo-pyridine with R¹ and R⁵]

| Ex. No. | R¹ | R⁵ |
|---------|-----|-----|
| 5 | H | CH₃ |
| 6 | H | Ph |
| 7 | CH₃ | H |
| 8 | CH₃ | CH₃ |
| 9 | CH₃ | Ph |
| 10 | CH₂Ph | H |

[where Ph represents phenyl]

EXAMPLE 11

1H-Pyrrolo [3,2-c]pyridine (5-Azaindole)

a) 4-tert-Butoxycarbonylamino-3-methylpyridine A solution of 4-tert-butoxycarbonylaminopyridine (10.0 g, 51.5 mmol) in tetrahydrofuran (150 ml) was cooled to –30° C. and n-butyllithium (45.3 ml, 2.5M in hexane, 113.3 mmol) was added at such a rate as to keep the temperature below –20° C. The mixture was stirred at 0° C. for 3 hours, the slurry cooled to –70° C. and a solution of methyl iodide (8.77 g, 61.8 mmol) in tetrahydrofuran (25 ml) added. The mixture was warmed to 20° C. and stirred for 1 hour. The mixture was quenched with water (100 ml) and extracted with ethyl acetate (2×100 ml). The combined ethyl acetate fractions were washed with saturated brine (100 ml), dried (Na₂SO₄), filtered and concentrated in vacuo. The crude product was chromatographed on silica gel (95% methylene chloride/5% methanol) and then swished in hot hexane to afford the title compound as a pale yellow solid; yield: 5.75 g (54%). mp 124°–126° C.; Analysis Found: C, 63.35; H, 7.72; N, 13.44. $C_{11}H_{16}N_2O_2$: requires C, 63.44; H, 7.74; N, 13.45%; ¹H NMR (CD₂Cl₁/TMS) δ1.52 (9H, s), 2.22 (3H, s), 6.92 (1H, br.s), 7.97 (1H, d, J=5.6 Hz), 8.28 (1H, s), 8.33 (1H, d, J=5.6 Hz).

b) 1H-Pyrrolo[3,2-c]pyridine

A solution of 4-tert-butoxycarbonylamino-3-methylpyridine (step (a), 1.0 g, 4.8 mmol) in tetrahydrofuran (40 ml) was cooled to –40° C. and tert-butyllithium (8.0 ml 1.7M in pentane, 13.6 mmol) added at such a rate as to keep the temperature below –30° C. The dark orange mixture was stirred at –40° C. for 1 hour and then treated with dimethylformamide (0.56 ml, 7.2 mmol). The mixture was warmed to 20° C. and stirred for 1 hour. 5.5M hydrochloric acid (15 ml) was added and the mixture heated at 45°–50° C. for 1 hour. The mixture was cooled to 0° C., isopropyl acetate (25 ml) added and the whole neutralised with 5M sodium hydroxide (15 ml). The phases were separated and the aqueous layer was extracted with isopropyl acetate (25 ml). The combined organic fractions were washed with saturated brine (25 ml), dried (Na₂SO₄), filtered and concentrated, in vacuo, to residue. The crude product was purified by chromatography on silica gel (95% methylene chloride/5% methanol) to afford the title compound as an off-white solid; yield: 0.45 g (79%). mp. 108°–110° C. [Lit. mp 109°–110° C.].

EXAMPLE 12

2-Phenyl-1H-pyrrolo[3,2-c]pyridine (2-Phenyl-5-azaindole)

4-tert-Butoxycarbonylamino-3-methylpyridine (Example 11a, 1.0 g, 4.8 mmol) was dilithiated with t-butyllithium and treated with N-methoxy-N-methylbenzamide (0.95 g, 5.76 mmol) as described previously. The crude product was purified by trituration with ethyl acetate to afford the title compound as a pale beige solid; yield: 0.59 g (63%); mp 276°–278°C.[Lit. mp 282°–283° C.].

EXAMPLE 13

1H-Pyrrolo[2,3-c]pyridine (6-Azaindole)

a) 3-tert-Butoxycarbonylamino-4-methylpyridine

A solution of 3-tert-butoxycarbonylaminopyridine (13.5 g, 69.5 mmol) in tetrahydrofuran (300 ml) was cooled to –70° C. and treated with tert-butyllithinum (102.2 ml, 1.7M in pentane, 173.7 mmol) at such a rate as to maintain the temperature at below –60° C. The mixture was aged at –60° C. to –70° C. for 3.5 hours and then treated with a solution of methyl iodide (11.2 g, 79.1 mmol) in tetrahydrofuran (50 ml) while keeping the temperature below –60° C. The mixture was stirred at –50° C. to –60° C. for 30 minutes, warmed to –30° C. and quenched with water (300 ml). The mixture was extracted with ethyl acetate (2×300 ml) and the combined organic fractions were washed with saturated brine (200 ml), dried (Na₂CO₃), filtered and concentrated in vacuo to residue. The crude product was purified by chromatography on silica gel (50% ethyl acetate/50% hexane) and swished in hot hexane to afford the title compound as a pale beige crystalline solid; yield: 7.34 g (51%); mp. 91°–93° C.; Analysis Found: C, 63.44; H, 7.72; N, 13.38. $C_{11}H_{16}N_2O_2$ requires C, 63.44; H, 7.74; N, 13.45%. ¹H NMR (CD₂Cl₂/TMS) δ1.50 (9H, s), 2.26 (3H, s), 7.12 (2H, d+br.s, J=5.0 Hz), 8.22 (1H, d, J=5.0 Hz), 8.80 (1H, s).

b) 1-tert-Butoxycarbonyl-2-hydroxy-6-azaindoline

A solution of 3-tert-butoxycarbonylamino-4-methylpyridine (step a, 1.47 g, 7.06 mmol) in tetrahydrofuran (50 ml) was cooled to –70° C. and treated with n-butyllithinum (6.2 ml, 2.5M in hexane, 15.5 mmol) at such a rate as to keep the temperature below –60° C. On complete addition the mixture was warmed to –20° C. and stirred for 30 minutes. The mixture was cooled to –30° C. and treated with dimethylformamide (0.66 ml, 8.47 mmol). The mixture was allowed to warm to 20° C., quenched with water (50 ml) and extracted with ethyl acetate (50 ml and 2×25 ml). The combined organic fractions were washed with saturated brine (50 ml), dried (Na₂SO₄), filtered and concentrated to residue in vacuo. The residue was purified by chromatography on silica gel (75% ethyl acetate/25% hexane) to afford the title compound as a colourless oil; yield: 1.26 g (81%) ¹H NMR (CD₂Cl₂/TMS): δ=1.6 (9H, s), 2.96 (1H, d, J=18 Hz), 3.35 (1H, dd, J=8 Hz & 18 Hz), 5.05 (1H, br.s), 5.98 (1H, br.s), 7.16 (1H, d, J=5 Hz), 8.15 (1H, d, J=5 Hz), 8.75 (1H, br.d).

c) 1H-Pyrrolo[2,3-c]pyridine

The azaindoline (step b, 1.1 g, 5.0 mmol) was dissolved in tetrahydrofuran (20 ml) and treated with 5.5M hydrochloric acid (5 ml). The mixture was heated at 50° C. for 4.5 hours cooled to 0° C. and basified with 5M sodium hydroxide (7.0 ml). The mixture was extracted with ethyl acetate (2×20 ml) and the combined ethyl acetate fractions were washed with saturated brine (20 ml), dried ($Na_2SO_4$), filtered and concentrated in vacuo to afford the title compound as a pale yellow crystalline solid; yield: 0.57 g (97%). mp. 132°–134° C.[Lit. mp 131°–132° C.].

EXAMPLE 14

2-Phenyl-1H-pyrrolo[2,3-c]pyridine (2-Phenyl-6-azaindole)

The dianion of 3-tert-butoxycarbonylamino-4-methylpyridine (Example 13a, 1.0 g, 4.8 mmol) was prepared with n-butyllithium and treated with N-methoxy-N-methylbenzamide (1.1 ml, 7.22 mmol) as described above. The crude product was purified by chromatography on silica gel (50% ethyl acetate/50% hexane) to afford the intermediate N-tert-butoxycarbonyl-2-hydroxy-2-phenyl-6-azaindoline as a pale yellow oil; yield: 1.12 g (75%).

$^1$H NMR ($CD_2Cl_2$/TMS):δ=1.48 (9H, s), 4.32 (2H, s), 7.13 (1H, d, J=5 Hz), 7.30 (1H, br.s), 7.50–8.04 (5H, m), 8.27 (1H, d, J=5 Hz), 8.84 (1H, s).

Treatment of the substituted azaindoline (1.05 g, 3.36 mmol) with 5.5M hydrochloric acid as above afforded a crude product that on trituration with ethyl acetate gave the title compound as an off white solid; yield: 0.43 g (66%). mp 222°–224° C. [Lit. mp 223°–225° C.].

EXAMPLE 15

2-Methyl-1H-pyrrolo[2,3-b]pyridine a) 2-tert-Butoxycarbonylamino-3-methylpyridine To a stirred solution of di-tert-butyldicarbonate (163.1 g, 748 mmol) in petrol (60°–80°) (100 ml) at reflux was added a solution of 2-amino-3-methylpyridine (50 g, 463 mmol) in ethyl acetate (25 ml) over 45 minutes. When addition was complete the reaction was stirred at reflux for a further 15 minutes, then allowed to cool to room temperature during which it solidified. The mixture was diluted with petrol (60°–80°) (150 ml) and filtered. The solid was washed with a further portion of petrol and dried to give the title compound as a white solid (65.9 g, 68%). $δ_H$ ($CDCl_3$) 1.44 (9H, s, OC($CH_3$)$_3$), 2.22 (3H, s, ArCH$_3$), 6.93–6.98 (1H, m, 5-H), 7.44 (1H, d, J 9.5 Hz, 4H), 8.19 (1H, d, J 4.8 Hz, 6H).

b) 2-Methyl-1H-pyrrolo[2,3-b]pyridine

To a mixture of the foregoing pyridine (10.4 g, 50 mmol) in tetrahydrofuran at −20° C. was added a solution of n-butyllithium (1.6M in hexanes, 68.8 ml, 110 mmol) keeping the temperature below −10° C. The resulting deep red solution was stirred at −15° C. for 30 minutes, after which ethyl acetate (5.9 ml, 60 mmol) was added to give a pale yellow solution with the temperature rising to 10° C. The reaction was warmed to room temperature, stirred for 1 hour and then quenched by addition of water (5 ml). Concentrated hydrochloric acid (30 ml) was added and the mixture stirred during which an exotherm and effervescence were observed. When the effervescence had subsided, the mixture was stirred for a further 2 hours. The two layers were separated, the aqueous phase basified with aqueous sodium hydroxide (4N) and extracted with ethyl acetate (3×50 ml). The combined extracts were washed with saturated brine (50 ml), dried ($MgSO_4$), treated with silica and evaporated in vacuo. The residue was chromatographed on silica eluting with 40% ethyl acetate/petrol (60°–80° C.) to yield the title compound as a pale yellow solid (1.9 g, 28%). $δ_H$ ($CDCl_3$) 2.55 (3H, s, ArCH$_3$), 6.17 (1H, s, 3-H), 7.00–7.05 (1 H, m, 5-H), 7.81 (1H, dd, J 11.1, 2.1 Hz, 4-H), 8.21 (1 H, dd, J 7.0, 2.1 Hz, 6-H), 11.88 (1H, br s, NH).

We claim:

1. A process for the preparation of 7-azaindole derivatives which comprises:

(i) deprotonation carried out at a temperature between −15° C. and +15° C. using 2 or more equivalents of an alkyllithium reagent of a compound of formula (I):

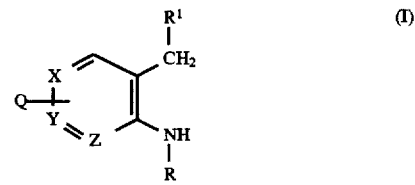

wherein

Q is hydrogen, $C_{1-6}$alkyl, $C_{2-6}$alkenyl, $C_{1-6}$alkoxy, hydroxy, aryl or aryl$C_{1-4}$alkyl; wherein aryl is unsubstituted or substituted phenyl or pyridyl, which can be substituted with one or two of $C_{1-6}$alkyl, $C_{2-6}$alkenyl, $C_{1-6}$alkoxy or hydroxy;

Z is —N= and X and Y are —CH=;

R is —CO(O)$C_{1-6}$alkyl or —C(O)$C_{1-6}$alkyl; and $R^1$ is hydrogen, $C_{1-6}$alkyl, $C_{2-6}$alkenyl or $C_{1-6}$alkyl substituted by a group selected from aryl or —NR$^2$R$^3$ where $R^2$ and $R^3$ each independently represent $C_{1-4}$alkyl, or $R^2$ and $R^3$, together with the nitrogen atom to which they are attached, form a 4–7 membered saturated heterocyclic ring, optionally containing in the ring an oxygen or sulphur atom or a group NR$^4$ where $R^4$ is $C_{1-4}$alkyl, aryl or aryl$C_{1-4}$alkyl; wherein aryl is defined above;

(ii) reaction carried out at a temperature between −15° C. and +40° C. of the product of step (i) with an amide of formula (IIA) or an ester of formula (IIB):

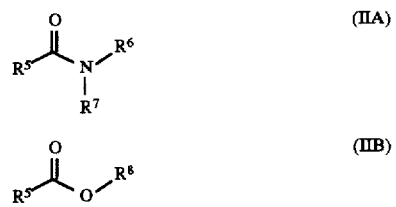

wherein $R^5$ is a hydrogen atom or a group selected from $C_{1-6}$alkyl or aryl; and $R^6$ is $C_{1-6}$alkyl;

$R^7$ is $C_{1-6}$alkyl, $C_{1-6}$alkoxy or aryl; and $R^8$ is $C_{1-6}$alkyl, aryl$C_{1-4}$alkyl or aryl; wherein aryl is defined above;

(iii) reaction of the product of step (ii) with a concentrated acid to give an 7-azaindole derivative of formula (III):

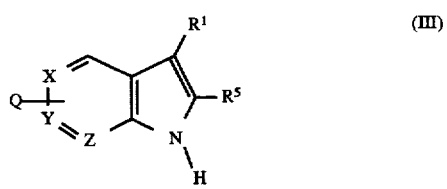

wherein Q, X, Y, Z, $R^1$ and $R^5$ are as previously defined.

2. A process as claimed in claim 1 for the preparation of acid salts of 7-azaindole derivatives which comprises steps (i) to (iii) as defined in claim 1 together with the step:

(iv) isolating the product of step (iii) as a crystalline solid by reaction with an acid to form the corresponding salt.

3. A process as claimed in claim 1 wherein the alkyllithium reagent of use in step (i) is selected from n-butyllithium and n-hexyllithium.

4. A process as claimed in claim 3 wherein between 2 and 3 equivalents of alkyllithium is used.

5. A process as claimed in claim 1 wherein step (ii) is effected using an amide of formula (IIA).

6. A process as claimed in claim 1 wherein the acid used in step (iii) is selected from hydrochloric acid, sulphuric acid, phosphoric acid, trifluoroacetic acid and methanesulphonic acid.

7. A process as claimed in claim 6 wherein 3M to 5.5M acid is used.

8. A process as claimed in claim 1 wherein the product of step (ii) is added to the acid in step (iii).

9. A process as claimed in claim 1 wherein the reaction temperature in step (iii) is maintained between 0° and 55° C. and, when the quench is complete, the temperature is then allowed to rise to between 40° C. and 55° C.

10. A process as claimed in claim 2 wherein the acid in step (iv) is any acid with a pKa of less than or equal to 3.0.

11. A process as claimed in claim 10 wherein the acid is selected from DL-tartaric acid, D-tartaric acid, L-tartaric acid, maleic acid, methanesulphonic acid, p-toluenesulphonic acid and hydrochloric acid.

12. A process as claimed in claim 2 wherein crystallisation in step (iv) is effected by dissolving the product of step (iii) in an organic solvent selected from isopropyl acetate (IPAC), acetone or ethanol or a mixture thereof, a warm solution of the organic acid in ethanol or water is then added and the mixture stirred at a temperature between 0° C. and room temperature to effect crystallisation.

13. A process as claimed in claim 2 wherein the free base is subsequently liberated by reaction with 5M sodium hydroxide solution.

14. A process as claimed in claim 1 wherein Q is a hydrogen atom.

15. A process as claimed in claim 1 wherein $R^1$ is a hydrogen atom.

16. A process as claimed in claim 1 wherein R is —CO(O)-tert-butyl or —C(O)-tert-butyl.

17. A process as claimed in claim 1 where, in the compounds of formula (IIA), $R^5$ is a hydrogen atom.

18. A process as claimed in claim 1 where, in the compounds of formula (IIA), $R^6$ is $C_{1-3}$alkyl and $R^7$ is $C_{1-3}$alkyl or $C_{1-3}$alkoxy.

19. A process as claimed in claim 1 where, in the compounds of formula (IIB), $R^5$ is a hydrogen atom or a methyl group.

20. A process as claimed in claim 1 where, in the compounds of formula (IIB), $R^8$ is a $C_{1-3}$alkyl group.

* * * * *